United States Patent [19]

Brandes et al.

[11] 4,156,001
[45] May 22, 1979

[54] SYNERGISTIC FUNGICIDAL COMPOSITIONS CONTAINING 1,2,4-TRIZOLE DERIVATIVES AND 2,4-DICHLORO-6-(O-CHLOROANILINO)-1,3,5-TRIAZINE

[75] Inventors: Wilhelm Brandes, Cologne; Paul-Ernst Frohberger; Hans Scheinpflug, both of Leverkusen; Wolfgang Kramer, Wuppertal, all of Fed. Rep. of Germany

[73] Assignee: Bayer Aktiengesellschaft, Leverkusen, Fed. Rep. of Germany

[21] Appl. No.: 870,403

[22] Filed: Jan. 18, 1978

Related U.S. Application Data

[62] Division of Ser. No. 742,039, Nov. 15, 1976.

[30] Foreign Application Priority Data

Nov. 26, 1975 [DE] Fed. Rep. of Germany ....... 2552967

[51] Int. Cl.² .......................... A01N 9/00; A01N 9/22
[52] U.S. Cl. ...................................... 424/249; 424/269
[58] Field of Search ............................... 424/269, 249

[56] References Cited

U.S. PATENT DOCUMENTS

| 3,972,891 | 8/1976 | Kramer et al. ...................... 424/269 |
| 3,972,892 | 8/1976 | Buchel et al. ....................... 424/269 |
| 3,983,240 | 9/1976 | Buchel et al. ....................... 424/269 |
| 3,993,765 | 11/1976 | Buchel et al. ...................... 424/269 |

OTHER PUBLICATIONS

Chem. Abst. 75, 116,074(e) (1971), Matsumae et al.
Chem. Abst. 71, 21141(c) (1969), Jones et al.
Chem. Abst. 73, 34096(h) (1970), Turner et al.

*Primary Examiner*—Albert T. Meyers
*Assistant Examiner*—D. W. Robinson
*Attorney, Agent, or Firm*—Sprung, Felfe, Horn, Lynch & Kramer

[57] ABSTRACT

Synergistic fungicidal compositions comprising

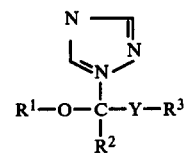

(I)

in which
  $R^1$ is optionally substituted phenyl,
  $R^2$ is hydrogen, alkyl or phenyl,
  $R^3$ is alkyl, cycloalkyl, phenyl or chlorophenyl, and
  Y is a keto group or a functional derivative thereof,
  and at least one member selected from the group consisting of
  (a) dithiocarbamates,
  (b) N-polyhaloalkylthio-amines or -amides,
  (c) imidazole and benzimidazole derivatives,
  (d) optionally nitrated polyhalobenzenes,
  (e) N-sulphinyl-N'-aryl-hydrazines, and
  (f) sulphur or alkaline earth metal polysulphides.

7 Claims, No Drawings

SYNERGISTIC FUNGICIDAL COMPOSITIONS CONTAINING 1,2,4-TRIZOLE DERIVATIVES AND 2,4-DICHLORO-6-(O-CHLOROANILINO)-1,3,5-TRIAZINE

This is a division of application Ser. No. 742,039 filed Nov. 15, 1976 now pending.

The present invention relates to new fungicidal synergistic combinations of certain 1,2,4-triazole derivatives and certain other fungicidal active compounds.

It has been disclosed in U.S. Pat. No. 3,912,752 that 1,2,4-triazole derivatives, such as, for example, 1-(p-chlorophenoxy)-3,3-dimethyl-1-(1,2,4-triazol-1-yl)-2-butanone and the corresponding 3,4-dichlorophenoxy derivative, exhibit a good action against Ascomycetes and Basidiomycetes, the action against powdery mildew fungi deserving special mention, and also against rust diseases and smut diseases of various crop plants.

The following fungicidal active compounds or groups of active compounds have also been disclosed:

dithiocarbamates, such as, for example, zinc dimethyldithiocarbamate ("ZIRAM") and manganese ethylene-1,2-bis-dithiocarbamate ("MANEB"), as well as 3-pyrrolidin-1-yl-propyldithiocarbamic acid;

polyhalogenoalkylthio derivatives, such as, for example, N-trichloromethylthio-tetrahydrophthalimide ("CAPTAN"), N-trichloromethylthio-phthalimide ("FOLPET") and N,N-dimethyl-N'-phenyl-N'-N'-fluorodichloromethylthio-sulphamide ("DICHLOFLUANID"), and the N'-4-methylphenyl compound analogous to the latter;

imidazole and benzimidazole derivatives, such as, for example, 2-methyl-5-(2',6'-dimethylphenylhydrazono)-imidazolenine and 2-[2',5'-dimethylpyrazol-1-yl]-1-phenyl-1-isopropylprop-2-yne;

polyhalogenobenzenes, such as, for example, pentachloronitrobenzene;

N-sulphinyl-N'-aryl-hydrazines, such as, for example, N-sulphinyl-N'-(3-chloro-4-trifluoromethyl-phenyl)-hydrazine; and sulphur, and compounds which eliminate sulphur.

The compounds, and groups of compounds, which have been mentioned are known. As regards dithiocarbamates, polyhalogenoalkylthio derivatives, polyhalogenobenzenes, sulphur and sulphur-eliminating compounds, data are to be found in R. Wegler "Chemie der Pflanzenschutz- und Schädlingsbekämpfungsmittel" ("Chemistry of Plant Protection Agents and Pesticides"), volume 2, pages 45 to 150, Heidelberg (1970); regarding the imidazole and benzimidazole derivatives, see German Offenlegungsschriften (German Published Specifications) Nos. 2,129,524, 2,130,030 and 2,128,700; regarding the N-sulphinyl-N'-aryl-hydrazines, see German Offenlegungsschrift (German Published Specification) No. 2,244,616.

The activity of the previously known active compounds is not fully satisfactory in all cases if these compounds are employed as individual components.

The present invention now provides a fungicidal composition containing as active ingredients (1) at least one 1,2,4-triazole derivative of the general formula

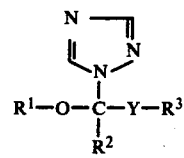

in which
R¹ represents phenyl which can optionally be substituted by halogen, nitro, trifluoromethyl, alkyl with up to 6 carbon atoms, alkoxy with up to 4 carbon atoms or phenyl,
R² represents hydrogen, alkyl with up to 4 carbon atoms or phenyl,
R³ represents alkyl with up to 6 carbon atoms, cycloalkyl with 5 or 6 carbon atoms, phenyl or 4-chlorophenyl and
Y represents a group of the formula CO, C=N-OH, C(OH)₂ or CH(OH), and (B) at least one compound selected from
(a) dithiocarbamates of the general formula

in which
R⁴ and R⁵ each independently represents an optionally substituted aliphatic radical and
X represents hydrogen, one equivalent of a metal atom or the radical (CH₃)₂N-CS-S,
(b) polyhalogenoalkylthio derivatives of the general formula

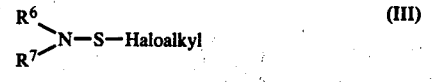

in which
R⁶ and R⁷ each independently represents alkyl, aryl, alkylcarbonyl, arylcarbonyl, alkylsulphonyl, arylsulphonyl, amidosulphonyl, alkylamidosulphonyl, dialkylamidosulphonyl, amidocarbonyl, alkylamidocarbonyl or dialkylamidocarbonyl or
R⁶ and R⁷, conjointly with the connecting nitrogen atom, represent an optionally substituted heterocyclic ring, and
Haloalkyl represents alkyl with up to 2 carbon atoms substituted by 2 to 5 halogen atoms,
(c) imidazole and benzimidazole derivatives of the general formula

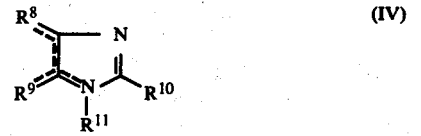

in which
R⁸ and R⁹ each independently represents hydrogen, an optionally substituted alkyl, aryl or arylhydrazo radical, or
R⁸ and R⁹ conjointly represent the group

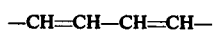

thereby forming a ring system which can optionally be substituted, $R^{10}$ represents hydrogen or an alkyl, aryl, heteroaryl, aralkyl or alkoxycarbonylamino radical, which radical can optionally be substituted, and $R^{11}$ represents hydrogen or an alkyl, aryl, aralkyl, aralkenyl, aralkynyl or alkylaminocarbonyl radical, which radical can be substituted or $R^{11}$ can be absent, (d) polyhalogenobenzenes of the general formula

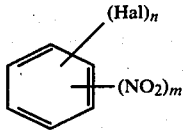

in which

Hal independently represents fluorine, chlorine or bromine, n represents 3, 4, 5 or 6 and m represents 0, 1, 2 or 3, but n and m together must not be greater than 6, (e) N-sulphinyl-N'-aryl-hydrazines of the general formula

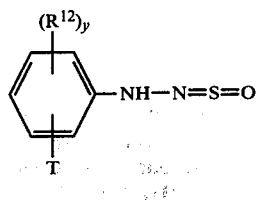

in which $R^{12}$ independently represents methyl, trifluoromethyl, methoxy or halogen, T represents trifluoromethyl or trifluoromethoxy and y represents 0, 1 or 2, and (f) sulphur or compounds which eliminate sulphur, alone or in admixture with a solid or liquid or liquefied gaseous diluent or carrier.

Surprisingly, the fungicidal action of the active compound combinations according to the invention is substantially greater than the action of the individual components and also than the expected sum of the individual components. The addition of active compounds from the abovementioned groups (a), (b), (c), (d), (e) and (f) to the 1,2,4-triazole derivatives of the formula (I) represents an enrichment of the art.

The 1,2,4-triazole derivatives to be used for the combination according to the invention are defined by the general formula (I). In this formula $R^1$ represents phenyl, which is preferably substituted by fluorine, chlorine, nitro, trifluoromethyl, methyl, methoxy or phenyl especially 4-phenyl, $R^2$ preferably represents hydrogen, $R^3$ preferably represents straight-chain or branched alkyl with 1 to 4 carbon atoms, phenyl or 4-chlorophenyl and Y has the preferred meanings CO or CH(OH). Typical examples of known compounds of the formula (I) are 1-(p-chlorophenoxy)-3,3-dimethyl-1-(1,2,4-triazol-1-yl)-2-butanone and the corresponding 3,4-dichlorophenoxy compound. The triazoles can be employed per se or in the form of their salts as described in U.S. Pat. No. 3,912,752.

The dithiocarbamates (group (a)) which can be used as components of the mixtures are defined by the formula (II). In this formula, $R^4$ preferably represents alkyl with up to 4 carbon atoms, optionally substituted by an —NH—CS—S— group, by an amino, $C_1$-$C_4$ alkylamino or di-($C_1$-$C_4$-alkyl)amino group or by a cyclic amine group. $R^5$ preferably represents hydrogen, methyl or ethyl. X preferably represents the dimethyldithiocarbamoyl radical, hydrogen or one equivalent of a heavy metal atom, such as zinc, manganese, iron or nickel or, if $R^4$ is —alkylene—NH—CS—S, two equivalents of the said metals. Typical examples of compounds of the formula (II) are: zinc N,N-dimethyldithiocarbamate ("ZIRAM"), manganese ethylene-1,2-bis-dithiocarbamate ("MANEB"), zinc ethylene-1,2-bis-dithiocarbamate ("ZINEB"), zinc propylene-1,2-bis-dithiocarbamate ("PROPINEB"), the co-ordination compound formed from manganese ethylene-1,2-bis-dithiocarbamate and zinc ions ("MANCOZEB"), tetramethylthiuram disulphide ("THIRAM", "TMTD") and 3-pyrrolidin-1-yl-propyl-dithiocarbamic acid, disclosed in Pat. No. 2,971,884 and German Offenlegungsschrift (German Published Specification) No. 2,415,059.

The polyhalogenoalkylthio derivatives (group (b)) which can be used as components of the mixtures are defined by the general formula (III). In this formula, the alkyl moieties of $R^6$ and $R^7$ advantageously each have up to 4 carbon atoms and the aryl moieties are phenyl, e.g. alkyl and/or halogeno-phenyl. $R^6$ preferably represents amidosulphonyl or dimethylamidosulphonyl and $R^7$ preferably represents phenyl, methylphenyl or halogenophenyl, or $R^6$ and $R^7$ conjointly preferably represent the radical

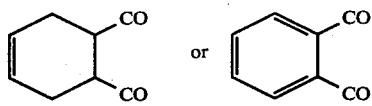

Typical examples of compounds of the general formula (III) are: N-trichloromethylthio-tetrahydrophthalimide ("CAPTAN"), N-trichloromethylthiophthalimide ("FOLPET"), N,N-dimethyl-N'-phenyl-N'-fluorodichloromethylthio-sulfamide ("DICHLOFLUANID"), N-(1,1,2,2-tetrachloroethylthio)-tetrahydrophthalimide ("CAPTAFOL") and N,N-dimethyl-N'-4-methylphenyl-N'-fluorodichloromethyl-thiosulphamide, disclosed in German Patent Specification No. 1,193,498.

The imidazole and benzimidazole derivatives (group (c)) which can be used as components of the mixtures are generally defined by the formula (IV). In this formula, the alkyl and aryl moieties are advantageously as defined for $R^6$ and $R^7$. $R^8$ and $R^9$ preferably represent hydrogen, alkyl with up to 4 carbon atoms, an optionally $C_{1-4}$-alkyl-substituted phenylhydrazo group or, conjointly, preferably the —CH=CH—CH=CH—. $R^{10}$ preferably represents hydrogen, alkyl with up to 4 carbon atoms, a heterocyclic five-membered ring with oxygen, sulphur and/or up to two nitrogen atoms as hetero-atoms, which heterocyclic ring can be methyl-substituted, and also, peferably, alkoxycarbonyl with a total of up to 5 carbon atoms. $R^{11}$ peferably represents hydrogen, or alkyl, alkenyl or alkynyl, each with up to 8 carbon atoms, and the said radicals, which can be straight-chain or branched, can also be phenyl-substituted, or $R^{11}$ preferably represents alkylaminocarbonyl, substituted by a CN group, having a total of 2 to 7 carbon atoms; finally, depending on the position of the double bonds on the ring system, the substituent $R^{11}$ can also be absent. Typical examples of compounds of the general formula (IV) are: 2-methyl-5-(2',6'-dimethylphenylhydrazono)-imidazolenine, 2-[2',5'-dimethylpyrazol-1'-yl]-benzimidazole and 1-[imidazol-1'-yl]-1-phenyl-1-isopropyl-prop-2-yne from German Offenlegungsschriften (German Published Specifications) Nos. 2,129,524, 2,130,030 and 2,128,700, 1-(N-butylcarbamoyl)-2-(methoxycarbonylamino)-benzimidazole ("BENOMYL"), 2-(methoxy-carbonylamino)-benzimidazole ("BMC", "CARBENDAZIM") from U.S. Pat. No. 3,657,443, 2-(2'-benzimidazole ("THIABENDAZOL") and 1-(5-cyanopentyl-carbamoyl)-2-(methoxycarbonylamino)-benzimidazole ("CYPENDAZOL") from German Offenlegungsschrift (German Published Specification) No. 1,812,005; and the remaining compounds are generally known and are to be found in standard works.

In place of those above-mentioned compounds of the group (c) which are derivatives of 2-aminobenzimidazole, it is also possible to employ compounds which are converted to 2-aminobenzimidazole derivatives under suitable conditions. Here there should be mentioned 1,1'-o-phenylene-bis-(3,3'-ethoxycarbonyl-thiourea)("THIOPHANATE") and the corresponding methoxycarbonyl compound, as well as yet further derivatives of o-phenylenediamine.

The polyhalogenobenzenes (group (d)) which can be used as compounds of the mixtures are defined by the general formula (V). In this formula, Hal preferably represents chlorine, n preferably represents 5 or 6 and m preferably represents 0 or 1, but n and m together must not be greater than 6. Compounds which may be mentioned as having been known world-wide for a long time are hexachlorobenzene and pentachloronitrobenzene ("QUINTOZEN").

In place of the above-mentioned compounds of the group (d) other active compounds, which contain at least 2 chlorine atoms on the nucleus, can also be used. Here there should be mentioned: tetrachloroisophthalodinitrile ("CHLOROTHALONIL"), 1,4-dichloro-2,5-dimethoxybenzene ("CHLORONEB") and 4,5,6,7-tetrachlorophthalide from U.S. Pat. No. 3,663,704.

The N-sulphinyl-N'-aryl-hydrazines (group (e)) which can be used as components of the mixtures are defined by the general formula (VI). In this formula, $R^{12}$ preferably represents chlorine and T preferably represents trifluoromethyl. An example to be mentioned is N-sulphinyl-N'-(3-chloro-4-trifluoromethyl-phenyl)-hydrazine. The compounds are known (see German Offenlegungsschrift (German Published Specification) No. 2,244,616).

Sulphur, or the sulphur-eliminating compounds (group (f)) which can be used as compounds of the mixtures have been known for a long time as fungicidally active materials. Sulphur-eliminating compounds which are used preferentially are the alkaline earth metal polysulphides, such as calcium polysulphide and barium polysulphide; the last-mentioned compounds, again, are generally known.

Instead of the preferred components of the mixtures, from groups (a), (b), (c), (d), (e) and (f), which according to the present invention are to be used in a mixture with the 1,2,4-triazole derivatives of the formula (I), it is also possible to use, as partners for the 1,2,4-triazole derivatives in the mixture: azo compounds, such as the sodium salt of p-dimethylaminophenyl-diazosulphonic acid ("FENAMINOSULF") and quinonoxime-benzoylhydrazone ("BENQUINOX"); guanidine derivatives, such as n-dodecylguanidine acetate ("DODINE"); triazino derivatives, such as 2,4-dichloro-6-(o-chloroanilino)-1,3,5-triazine ("ANILAZIN"); bis-trifluoromethylimino derivatives, such as 2-methylimino-3-(4'-chlorophenyl)-4,5-bis-(trifluoromethylimino)-thiazolidine; inorganic metal salts, such as, for example, inorganic copper compounds; metal-organic compounds, such as, for example, organic tin compounds and organic mercury compounds; organo-phosphorus derivatives, such as, for example, dithiolphosphoric acid O-ethyl-S,S-diphenyl ester ("EDIFENPHOS"), thiolphosphoric acid O,O-diethyl-S-benzyl ester, dithiolphosphoric acid O-butyl-S-ethyl-S-benzyl ester and benzenethiolphosphonic acid O-methyl-S-benzyl ester; oxathiines, such as 2,3-dihydro-6-methyl-1,4-oxathiine-5-carboxylic acid anilide and the cyclic sulphone derived from the latter compound; and anthraquinone derivatives, such as 2,3-dicyano-1,4-dithia-anthraquinone.

The active compounds mentioned in the preceding paragraph can also be added as a further component (for example as a third component) to a mixture of a 1,2,4-triazole derivative and an active compound from the groups (a) to (b).

The weight ratio of the groups of active compounds in the active compound combinations can vary within relatively wide ranges. In general, 0.1 to 500 parts by weight of active compound from active compound classes (a) to (f), preferably 0.2 to 200 and especially about 0.3 to 3.5 parts by weight from the latter classes, are present per part by weight of 1,2,4-triazole derivative.

The active compound combinations according to the invention exhibit a powerful fungitoxic action. They do not damage crop plants in the concentrations required for combating fungi and have a low toxicity to warm-blooded animals. For these reasons, they are suitable for use as plant protection agents for combating fungi and bacteria. Fungitoxic agents are employed in plant protection for combating *Plasmodiophoromycetes*, Chytridiomycetes, Oomycetes, Zygomycetes, Ascomycetes, Basidiomycetes and Deuteromycetes.

The active compound combinations according to the invention have a very broad spectrum of action and can be used against parasitic fungi which infest above-ground parts of plants or which attack the plants through the soil, and against seed-borne pathogens. Such active compound combinations are of particular practical importance as seed dressings used against phytopathogenic fungi which are borne with the seed or occur in the soil and infest the crop plants from there. What is concerned are seedling diseases, root rots and diseases of stalks, stems, leaves, blossoms, fruit and seeds which are caused, in particular, by species of Tilletia, Urocystis, Ustilago, Septoria, Typhula, Rhynchosporium, Helminthosporium and Fusarium. As a result of the systemic action of the component of the mixture, the plants are also frequently even protected for a long time after dressing, against pathogens which can attack various parts of the shoot, for example *Erysiphe graminis* and species of Puccinia. The active compound combinations can also be employed as soil treatment agents against phytopathogenic fungi and act against root rots and tracheomycoses which are caused, for example, by pathogens of the genera Pythium, Verticillium, Phialophora, Rhizoctonia, Fusarium and Thielaviopsis.

However, the active compound combinations according to the invention also exhibit an excellent action, when applied directly to the above-ground parts of plants, against pathogens present on various crop plants, such as powdery mildew fungi (species of Erysiphe, Uncinula, Sphaerotheca and Podosphaera, and *Leveillula taurica*), rust fungi, species of Venturia, species of Cercospora, species of Alternaria, species of Botrytis, species of Phytophthora, species of Peronospora, *Pyricularia oryzae* and *Pellicularia sesakii*.

The active materials according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active materials may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active materials is present in an amount substantially between about 0.1–95% by weight, and preferably 0.5–90% by weight, of the mixture, whereas carrier composition mixtures suitable for direct application or field application generally contemplate those in which the active material is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active material which is effective for the purpose in question and which is generally between about 0.0001–95%, and preferably 0.01–95%, by weight of the mixture.

The active materials can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active material or even the 100% active substance alone, e.g. about 20–100% by weight of the active material.

Especially when used as leaf fungicides, the active compound concentrations in the use forms can be varied within a fairly wide range. They are, in general, from 0.5 to 0.0005 percent by weight and preferably from 0.2 to 0.001 percent.

For the treatment of seed, amounts of active compound of 0.01 to 50 g per kilogram of seed, preferably 0.1 to 5 g, are generally required.

For the treatment of soil, amounts of active compound of 1 to 1,000 g per cubic meter of soil, preferably 10 to 200 g, are generally required.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following a greenhouse at 23°–24° C. and at a relative atmospheric humidity of about 75%.

After 12 days, the infection of the cucumber plants was determined. The assessment data were converted to percent infection. 0% means no infection; 100% that the plants were totally infected.

The active compounds, the concentrations of the active compounds and the results can be seen from the following table.

Table 1

| | Erysiphe test (cucumbers)/protective | | | |
|---|---|---|---|---|
| | Infection in % at an active compound concentration of | | | |
| Active compound | 0.01% | 0.005% | 0.000125% | 0.000062% |
| Known individual active compounds: | | | | |
| 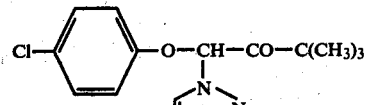 (1) | | | 25 | 41 |
| $(CH_3)_2N-SO_2-N-S-CFCl_2$ 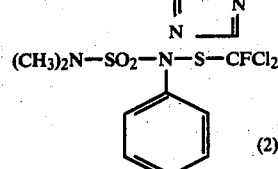 (2) | 87 | 100 | | |
| $(CH_3)_2N-SO_2-N-S-CFCl_2$ 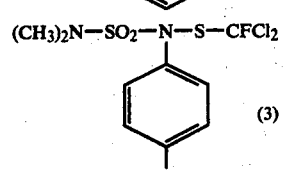 $CH_3$ (3) | 100 | 100 | | |
| Sulphur (4) | 66 | 100 | | |
| Mixtures according to the invention: | | | | |
| Mixture of (1) + (2) | | | | |
| Mixing ratio | 1:40 | 1:80 | 1:160 | |
| Concentration of (1) | 0.000125% | 0.000062% | 0.000062% | |
| Concentration of (2) | 0.005 % | 0.005 % | 0.01 % | |
| Infection | 12 | 25 | 29 | |
| Mixture of (1) + (3) | | | | |
| Mixing ratio | | 1:80 | 1:160 | |
| Concentration of (1) | | 0.000062% | 0.000062% | |
| Concentration of (3) | | 0.005 % | 0.01 % | |
| Infection | | 25 | 34 | |
| Mixture of (1) + (4) | | | | |
| Mixing ratio | | 1:80 | 1:160 | |
| Concentration of (1) | | 0.000062% | 0.000062% | |
| Concentration of (4) | | 0.005 % | 0.01 % | |
| Infection | | 29 | 25 | | examples:

EXAMPLE 1

Erysiphe test (cucumbers)/protective
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in

EXAMPLE 2

Fusicladium test (apple)/(protective)
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse for 14 days.

15 days after inoculation, the infection of the seedlings was determined. The assessment data were converted to percent infection. 0% means no infection; 100% means that the plants were totally infected.

The active compounds, the concentrations of the active compounds and the results can be seen from the following table:

Table 2

| Fusicladium test (apple)/(protective) | |
|---|---|
| Active compound | Infection in % at an active compound concentration of 0.00062% |
| Known individual active compounds: | |
| 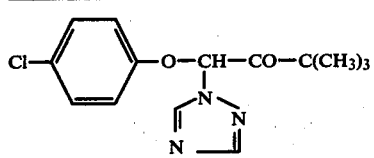 (1) | 17 |
| 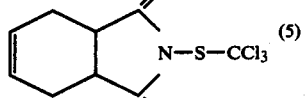 (5) | 30 |
| 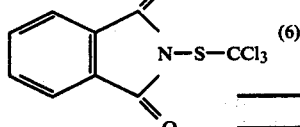 (6) | 16 |
| Mixtures according to the invention: | |
| Mixture of (1) + (5) | |
| Mixing ratio | 1:1 |
| Concentration of (1) | 0.00062% |
| Concentration of (5) | 0.00062% |

Table 2-continued

| Fusicladium test (apple)/(protective) | |
|---|---|
| Infection | 12 |
| Mixture of (1) + (6) | |
| Mixing ratio | 1:1 |
| Concentration of (1) | 0.00062% |
| Concentration of (6) | 0.00062% |
| Infection | 1 |

EXAMPLE 3

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C. in a refrigerator.

The germination of the spores on the wheat grains, each of which was contaminated with about 100,000 spores, was subsequently determined microscopically. The smaller the number of spores which had germinated, the more effective was the active compound.

The active compounds, the amounts of the active compounds used, and the percentage spore germination can be seen from the following table.

Table 3

| Seed dressing test/bunt of wheat | | |
|---|---|---|
| Active compounds | Amount of active compound used, in g/dt* of seed (*dt = decitonne = 100 kg) | Spore germination |
| no dressing | — | >10% |
| Known individual active compounds: | | |
| 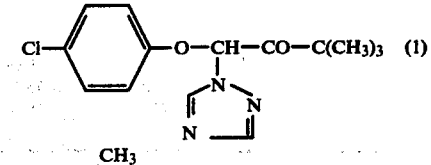 (1) | 100<br>50<br>25 | >10%<br>>10%<br>>10% |
| 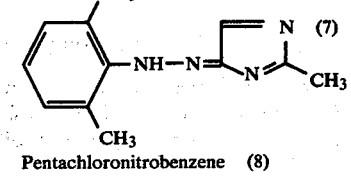 (7) | 30 | slight |
| Pentachloronitrobenzene (8) | 60<br>30 | slight<br>slight |
| [(CH₃)₂N—CS—S—]₂Zn (9) | 160 | slight |
| Mixtures according to the invention: | | |
| (1) + (7) | 25 + 30 | none |
| (1) + (8) | 25 + 25 | none |
| (1) + (9) | 50 + 160 | none |

EXAMPLE 4

Seed dressing test/bunt of wheat/field trial (seed-borne mycosis)

To produce a suitable dry dressing, the active compound was extended with a mixture of equal parts by weight of talc and kieselguhr to give a finely powdered mixture with the desired concentration of the active compound.

Dressing was effected in 4 individual portions each of 100 g, which were sown onto 4 plots of size 5 m². The percentages of infection which are quoted hereinafter were obtained by completely counting all diseased ears on the individual plots and estimating the total number of all ears from counting a few plots in which the growth was apparently equally dense.

For testing the action against bunt of wheat (*Tilletia caries*), winter wheat (certified seed), which had beforehand been contaminated with 2 g of chlamydospores per kg of seed, was used.

Dressing: beginning of October
Sowing: 10th to 20th October
Evaluation: end of June to middle of July The percentages of diseased ears were based in each case on about 2,000 ears per plot = a total of about 8,000 ears per experimental entry.

The active compounds, the amounts of active compound used and the number of diseased ears can be seen from the table which follows:

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Drechslera graminea* (previously *Helminthosporium gramineum*), was shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the

Table 4
Seed dressing test/bunt of wheat/ field trial

| Active compounds | Amount of active compound used in g/dt of seed | Number of ears infected with bunt, in % of the total number of ears |
|---|---|---|
| without dressing | — | 52.82 |
| Known individual active compounds: | | |
| 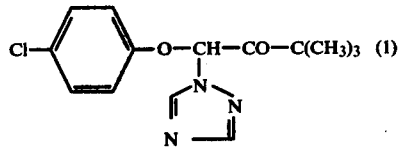 (1) | 50 | 0.67 |
| 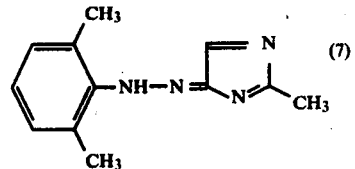 (7) | 60 | 2.39 |
| 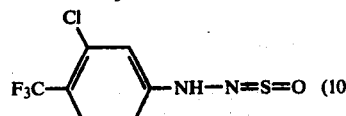 (10) | 40 | 0.34 |
| 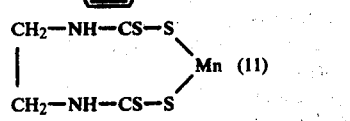 (11) | 100 | 0.56 |
| Pentachloronitrobenzene (8) | 20 | 0.1 |
| | 60 | 0.76 |
| 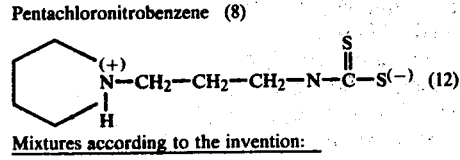 (12) | | |
| Mixtures according to the invention: | | |
| (1) + (7) | 50 + 30 | 0.12 |
| (1) + (10) | 50 + 20 | 0.02 |
| | 50 + 40 | 0.00 |
| (1) + (11) | 50 + 100 | 0.00 |
| (1) + (8) | 50 + 20 | 0.02 |
| (1) + (12) | 50 + 30 | 0.09 |
| | 50 + 60 | 0.01 |

EXAMPLE 5

Seed dressing test/stripe disease of barley (seed-borne mycosis)

more effective was the active compound.

The active compounds, the amounts of the active compounds used and the number of diseased plants can be seen from the following table:

Table 5

Seed dressing test/stripe disease of barley

| Active compound | Amount of active compound used in g/dt of seed | Number of plants with stripe disease in % of the total number of emerged plants |
| --- | --- | --- |
| no dressing | — | 55.7 |
| Known individual active compounds: | | |
| 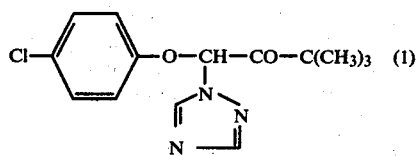 (1) | 50 | 20.0 |
| 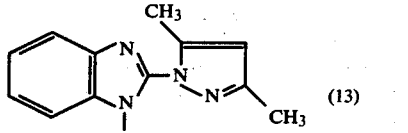 (13) | 40 | 2.1 |
| 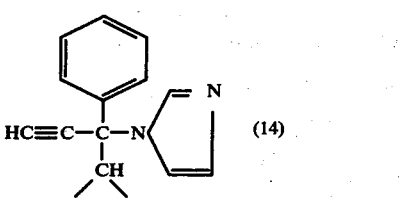 (14) | 30 | 4.1 |
|  | 20 | 6.3 |
| 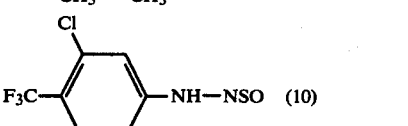 (10) | 40 | 2.0 |
| 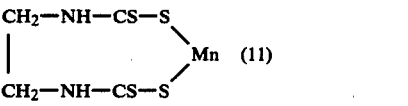 (11) | 100 | 9.1 |
| Mixtures according to the invention: | | |
| (1) + (13) | 50 + 40 | 0.0 |
| (1) + (14) | 50 + 30 | 0.0 |
|  | 50 + 15 | 0.0 |
| (1) + (10) | 50 + 40 | 0.0 |
| (1) + (11) | 50 + 100 | 2.1 |

EXAMPLE 6

Seed dressing test/stripe disease of barley/field trial (seed-borne mycosis)

To produce a suitable dry dressing, the active compound was extended with a mixture of equal parts by weight of talc and kieselguhr to give a finely powdered mixture with the desired concentration of the active compound.

Dressing was effected in 4 individual portions each of 100 g, which were sown onto 4 plots of size 5 m². The percentages of infection which are quoted hereinafter were obtained by completely counting all diseased stems on the individual plots and estimating the total number of all stems from counting a few plots in which the growth was apparently equally dense.

To test the action against stripe disease of barley, summer barley was used, which was naturally infected with *Drechslera graminea* (previously referred to as *Helminthosporium gramineum*).

Dressing: middle of February
Sowing: end of February
Evaluation: beginning of June The percentages of diseased stems were based in each case on about 2,000 stems per plot = a total of about 8,000 stems per experimental entry.

The active compounds, the amounts of active compound used and the number of diseased stems can be seen from the table which follows:

Table 6

Seed dressing test/stripe disease of barley/field trial

| Active compound | Amount of active compound used in g/dt of seed | Number of stems with stripe disease in % of the total number of stems |
| --- | --- | --- |
| no dressing | — | 59.29 |
| Known individual active compounds: | | |

Table 6-continued

Seed dressing test/stripe disease of barley/field trial

| Active compound | Amount | Result |
|---|---|---|
| 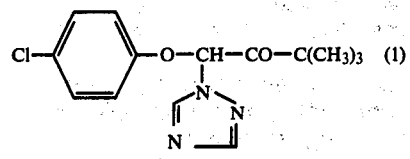 Cl—⌬—O—CH—CO—C(CH₃)₃ (1) with triazole | 50 | 14.51 |
| 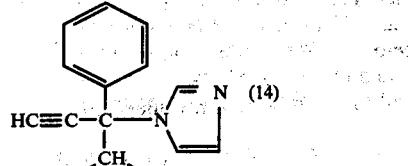 HC≡C—C(Ph)—N(imidazole), CH(CH₃)₂ (14) | 30 | 2.92 |
| CH₂—NH—CS—S\\<br>             Mn (11)<br>CH₂—NH—CS—S/ | 100 | 5.81 |
| Known individual active compounds: | | |
| 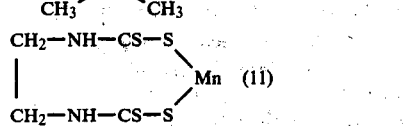 piperidine-N—CH₂—CH₂—CH₂—NH—CS—S (+/−) (12) | 60 | 0.88 |
| [(CH₃)₂N—CS—S—]₂Zn (9) | 160 | 26.25 |
| Mixtures according to the invention: | | |
| (1) + (14) | 50 + 30 | 0.47 |
| (1) + (11) | 50 + 100 | 2.48 |
| (1) + (12) | 50 + 30 | 0.45 |
|  | 50 + 60 | 0.04 |
| (1) + (9) | 50 + 160 | 10.47 |

EXAMPLE 7

Seed dressing test/*Septoria nodorum* on wheat (seed-borne mycosis)

To produce a suitable dry dressing, the active compound was extended with a mixture of equal parts by weight of talc and kieselguhr to give a finely powdered mixture with the desired concentration of active compound.

To apply the dressing, wheat seed, which was naturally infected by *Septoria nodorum*, was shaken with the dressing in a closed glass bottle. 2 batches of 100 grains of the seed were sown 1 cm deep in quartz sand in seed boxes and were cultivated in a greenhouse at temperatures of 15° C. The typical symptoms of *Septoria nodorum* developed over the course of 3 weeks.

After this time, the number of diseased plants was determined as a percentage of the total number of emerged plants. The fewer plants were diseased, the more effective was the active compound.

The active compounds, the amounts of the active compound used and the number of diseased plants can be seen from the following table:

Table 7

Seed dressing test/*Septoria nodorum* on wheat

| Active compound | Amount of active compound used in g/dt of seed | Number of diseased plants in % of the total number of emerged plants |
|---|---|---|
| no dressing | — | 95.0 |
| Known individual active compounds: | | |
| 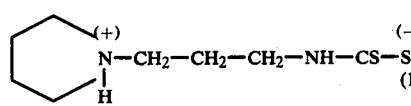 Cl—⌬—O—CH—CO—C(CH₃)₃ (1) | 75 | 12.4 |
| 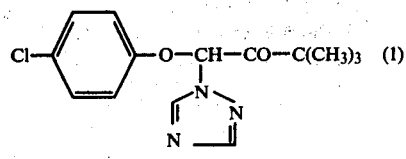 CH₂—NH—CS—S\\<br>             Zn (11)<br>CH₂—NH—CS—S/ | 80 | 35.8 |
| Mixture according to the invention: | | |
| (1) + (11) | 75 + 80 | 6.2 |

EXAMPLE 8

Seed dressing test/bunt of wheat (seed-borne mycosis)

To produce a suitable dry dressing, the particular active compound is extended with a mixture of equal parts by weight of talc nd kieselguhr to provide a finely powdered mixture with the desired final concentration of such active compound.

Wheat seed is contaminated with 5 g of the chlamydospores of *Tilletia caries* per kg of seed. To apply the given dressing, the seed is shaken with such dressing in a closed glass flask. The seed, on moist loam under a cover of a layer of muslin and 2 cm of moderatedly moist compost soil, is exposed to optimum germination conditions for the spores for 10 days at 10° C. in a refrigerator.

The germination of the spores on the wheat grains, each of which is contaminated with about 100,000 spores, is subsequently determined microscopically. The smaller the number of spores which have germinated, the more effective is given active compound.

The particular active compounds tested, their concentrations in the dressing, the amounts of dressing used and the percentage spore germination obtained can be seen from the following Table 8.

taken up in 25 parts by weight of dimethylformamide and 0.06 part by weight of Emulsifier W, and 975 parts by weight of water were added. The concentrate was diluted with water to the desired final concentration of the spray liquor.

To test the protective activity, young wheat plants of the Michigan Amber variety, having one leaf, were inoculated with a uredospore suspension of *Puccinia recondita* in 0.1% strenght aqueous agar. After the spore suspension had dried off, the wheat plants were sprayed with the preparation of active compound until dew-moist and were placed in a greenhouse to incubate for 24 hours at about 20° C. and 100% atmospheric humidity.

After leaving the plants for 10 days at a temperature of 20° C. and 80–90% atmospheric humidity, the occurrence of rust pustules on the plants was evaluated. The degree of infection was expressed in percent of the infection of the untreated control plants. 0% denotes no infection and 100% denotes the same degree of infec- Table 8

| Seed dressing test/bunt of wheat | | |
|---|---|---|
| Active compound | Amount of active compounds in g/dt* | Spore germination |
| undressed | | >10 |
| Known individual active compounds: | | |
| Cl—C₆H₄—O—CH(N₂C₂H)—CO—C(CH₃)₃ (1) | 25 | >10 |
| ANILAZIN | 25 | medium |
| Mixtures according to the invention: | | |
| (1) + ANILAZIN | 25 + 25 | weak |

*dt = deciton = 100 kg

EXAMPLE 9

Shoot treatment test/cereal rust/protective (leaf-destroying mycosis)

To produce a suitable preparation of active compound, 0.25 part by weight of active compound was tion as in the case of the untreated control. The lower the infection with rust, the more active is the compound being tested.

The active compounds, active compound concentrations in the spray liquor and degrees of infection can be seen from the Table 9 which follows:

Table 9

| Shoot treatment test/cereal rust/protective | | |
|---|---|---|
| Active compounds | Active compound concentration in the spray liquor, in % by weight | Infection in % of the untreated control |
| untreated | — | 100.0 |
| Known individual active compounds | | |
| Cl—C₆H₄—O—CH(N₂C₂H)—CO—C(CH₃)₃ (1) | 0.005 | 50.0 |

Table 9-continued

Shoot treatment test/cereal rust/protective

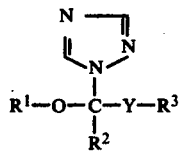
(ANILAZIN)         0.08         12.5

Mixtures according to the invention (1) + ANILAZIN     0.005 + 0.08     0.0

A mixture consisting of 1,2,4-triazole derivative, especially the 1-(p-chlorophenoxy)-3,3,-dimethyl-1-(1,2,4-triazol-1-yl)-2-butanone and the triazino derivative 2,4-dichloro-6-(o-chloroanilino)-1,3,5-triazine ("ANILAZIN") is suitable for combating diseases on the leaves and the ears of cereal crops, preferably in weight ratios of 12 to 20 parts by weight of ANILAZIN to one part by weight of 1,2,4-triazole derivative. This composition is effective against powdery mildew (*Erisyphe graminis*), rost diseases (*Puccinia striiformis* and *Puccinia recondita*) and Rhynchosphorium species, and also against important Septoria species (*Septoria nodorum, Septoria tritici*). Further, the composition is suitable for the simultaneous control of coffee rost disease (*Hemileia vastatrix*) and the coffee berry disease (*Colletotrichum coffeanum*), preferably in weight ratios from 1.5 to 12 parts by weight of ANILAZIN to one part by weight of 1,2,4-triazole derivative.

It will be appreciated that the instant specification and examples are set forth by way of illustration and not limitation, and that various modifications and changes may be made without departing from the spirit and scope of the present invention.

What is claimed is:

1. A fundicidal composition containing as active ingredients (A) 1,2,4-triazole derivative of the formula $$R^1-O-\underset{\underset{R^2}{|}}{\overset{\overset{N-\!\!\!=\!\!\!\underset{\|}{N}}{\underset{|}{N}}}{C}}-Y-R^3$$

in which

R$^1$ is phenyl, or phenyl substituted by halogen, nitro, trifluoromethyl, alkyl with up to 6 carbon atoms, alkoxy with up to 4 carbon atoms or phenyl, R$^2$ is hydrogen, alkyl with up to 4 carbon atoms or phenyl, R$^3$ is alkyl with up to 6 carbon atoms, cycloalkyl with 5 or 6 carbon atoms, phenyl or 4-chlorophenyl, and Y is CO, C(OH)$_2$ or CH(OH), and (B)

about 1 to 16 times by weight as much 2,4-dichloro-6-(o-chloroanilino)-1,3,5-triazine.

2. A composition according to claim 1, which contains (A) the 1,2,4-triazole wherein R$^1$ is phenyl optionally substituted by fluorine, chlorine, nitro, trifluoromethyl, methyl, methoxy or phenyl, R$^2$ is hydrogen, R$^3$ is alkyl with 1 to 4 carbon atoms, phenyl or 4-chlorophenyl, and Y is a CO or CH(OH) group, and (B) 1 to 16 parts per part by weight of component (A) of 2,4-dichloro-6-(O-chloroanilino)-1,3,5-triazine.

3. A fungicidal composition according to claim 2, wherein ingredient (A) is

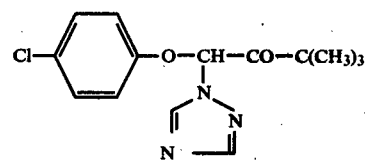

4. A method of combating fungi which comprises applying to the fungi, or to a habitat thereof, a fungicidally effective amount of a composition according to claim 1.

5. A method of combating fungi which comprises applying to the fungi, or to a habitat thereof, a fungicidally effective amount of a composition according to claim 3.

6. The method according to claim 4, in which the composition is applied to soil in a total amount of about 1 g to 1000 g of active material per cubic meter of soil.

7. The method according to claim 4, in which the composition is applied to seed in a total amount of about 0.01 g to 50 g of active material per kg of seed.

* * * * *